(12) United States Patent
Sasano et al.

(10) Patent No.: US 11,730,136 B2
(45) Date of Patent: Aug. 22, 2023

(54) ABSORBENT SHEET FOR PETS

(71) Applicant: UNICHARM CORPORATION, Ehime (JP)

(72) Inventors: Yasuhiro Sasano, Kanonji (JP); Satoshi Hasegawa, Edgewater, NJ (US); Takeshi Ikegami, Fort Lee, NJ (US)

(73) Assignee: Unicharm Corporation, Ehime (JP)

( * ) Notice: Subject to any disclaimer, the term of this patent is extended or adjusted under 35 U.S.C. 154(b) by 518 days.

(21) Appl. No.: 16/885,950

(22) Filed: May 28, 2020

(65) Prior Publication Data

US 2020/0288665 A1     Sep. 17, 2020

Related U.S. Application Data

(63) Continuation of application No. PCT/JP2018/043491, filed on Nov. 27, 2018.

(30) Foreign Application Priority Data

Nov. 29, 2017    (JP) ................................. 2017-229063

(51) Int. Cl.
    *A01K 1/01*          (2006.01)
    *A61F 13/511*       (2006.01)
    (Continued)

(52) U.S. Cl.
    CPC ...... *A01K 1/0107* (2013.01); *A61F 13/51104* (2013.01); *A61F 13/51394* (2013.01);
    (Continued)

(58) Field of Classification Search
    CPC ................ A01K 1/0107; A01K 1/0157; A61F 13/51104; A61F 13/51394;
    (Continued)

(56) References Cited

U.S. PATENT DOCUMENTS 4,761,322 A *   8/1988   Raley .................... D04H 1/559
                                                     156/553
4,961,930 A *   10/1990   Perdelwitz, Jr., .... A01K 1/0353
                                                    119/28.5

(Continued)

FOREIGN PATENT DOCUMENTS

JP          2001-352852 A     12/2001
JP          2003033381 A *   2/2003           A61F 13/45

(Continued)

OTHER PUBLICATIONS

International Search Report issued in corresponding International Application No. PCT/JP2018/043491 dated Feb. 26, 2019 (4 pages).

(Continued)

*Primary Examiner* — Arti Singh-Pandey
(74) *Attorney, Agent, or Firm* — Osha Bergman Watanabe & Burton LLP (57) ABSTRACT

An absorbent sheet for pets includes: a top sheet disposed on a top side of the absorbent sheet; a back sheet disposed on a back side of the absorbent sheet; and an absorbent body disposed between the top sheet and the back sheet, the absorbent body including: top recessed portions, each recessed toward the back side from the top side and comprising a top bottom portion; and back recessed portions, each recessed toward the top side from the back side and comprising a back bottom portion. At least some of the top bottom portions are located either: at the same position as some of the back bottom portions in a thickness direction, or closer to the back side than the back bottom portions in the thickness direction.

7 Claims, 8 Drawing Sheets

(51) Int. Cl.
*A61F 13/513* (2006.01)
*A61F 13/15* (2006.01)
*A61F 13/51* (2006.01)
*A61F 13/514* (2006.01)

(52) U.S. Cl.
CPC ............... *A61F 2013/15365* (2013.01); *A61F 2013/5149* (2013.01); *A61F 2013/51078* (2013.01); *Y10T 442/674* (2015.04)

(58) Field of Classification Search
CPC .. A61F 2013/15365; A61F 2013/51078; A61F 2013/5149
See application file for complete search history.

(56) References Cited

U.S. PATENT DOCUMENTS

| | | | |
|---|---|---|---|
| 10,274,433 B1* | 4/2019 | Betts-Lacroix | ............................. G01N 33/54373 |
| 2003/0015145 A1 | 1/2003 | Deg | |
| 2007/0107662 A1* | 5/2007 | Queen | ................ A47G 27/0206 119/28.5 |
| 2014/0336608 A1* | 11/2014 | Hao | ........................ A61F 13/45 428/156 |
| 2016/0074256 A1* | 3/2016 | Strube | .................... B32B 5/142 428/171 |
| 2016/0076184 A1* | 3/2016 | Orr | ................... A61F 13/53743 428/178 |
| 2016/0143248 A1* | 5/2016 | Bin | ...................... A01K 1/0155 119/172 |
| 2017/0290718 A1* | 10/2017 | Takiyama | ............. A61F 13/511 |
| 2019/0183692 A1* | 6/2019 | Cheng | .................. A01K 1/0157 |

FOREIGN PATENT DOCUMENTS

| | | | |
|---|---|---|---|
| JP | 2004-141077 | A | 5/2004 |
| JP | 3113878 | U | 9/2005 |
| JP | 2011-205970 | A | 10/2011 |
| JP | 2012-213337 | A | 11/2012 |
| JP | 2014-195412 | A | 10/2014 |

OTHER PUBLICATIONS

Written Opinion of the International Searching Authority issued in corresponding International Application No. PCT/JP2018/043491 dated Feb. 26, 2019 (4 pages).

Office Action issued in corresponding Chinese Patent Application No. CN 201880077257.3 dated Feb. 14, 2022 (19 pages).

Office Action issued in counterpart European Patent Application No. EP 18882486.6 dated Apr. 12, 2022 (5 pages).

Extended European Search Report issued in corresponding European Application No. 18882486.6 dated Oct. 23, 2020 (9 pages).

Office Action issued in corresponding Chinese Patent Application No. 201880077257.3 dated Jun. 29, 2021 (18 pages).

Office Action issued in counterpart Chinese Patent Application No. 201880077257.3 dated Jun. 20, 2022, with translation (15 pages).

* cited by examiner

ABSORBENT SHEET FOR PETS

CROSS-REFERENCE TO RELATED APPLICATIONS

The entire content of Japanese Patent Application No. 2017-229063 (filed on Nov. 29, 2017) is incorporated into the specification of the present application by reference.

TECHNICAL FIELD

The present invention relates to an absorbent sheet for pets for absorbing pets' excrement, for example, urine.

BACKGROUND ART

An absorbent sheet for pets for absorbing pets' excrement, for example, urine is known (refer to Patent Literature 1). The absorbent sheet for pets described in Patent Literature 1 has a liquid-impermeable back sheet, a liquid-permeable top sheet, and an absorbent body located between the back sheet and the top sheet. In the absorbent body, an embossed portion is formed.

PATENT LITERATURE

Patent Literature 1: Japanese Unexamined Patent Publication No. 2011-205970

An absorbent sheet for pets is used by an animal (pet) which is not by a purchaser (animal guardian), and the purchaser perceives the performance by the appearance and texture of the absorbent sheet for pets. Specifically, a purchaser perceives the absorption performance by the thickness of the absorbent sheet for pets and has secure feeling about the absorption performance by the thickness of the absorbent sheet for pets.

The embossed portion in Patent Literature 1 is recessed with respect to the top surface of the absorbent sheet for pets. Therefore, there is a case where, when seeing the absorbent sheet for pets from the top side, a purchaser checks the depth of the embossed portion and perceives the thickness of the absorbent sheet for pets. However, for the absorbent sheet for pets of Patent Literature 1, there has been a case where a purchaser has a difficulty in perceiving the thickness when touching the absorbent sheet for pets and the purchaser cannot sufficiently feel safe.

SUMMARY

One or more embodiments of the invention provide an absorbent sheet for pets that allows a purchaser to perceive the thickness of the absorbent sheet for pets and easily feel safe about the absorption performance.

A absorbent sheet for pets according to one or more embodiments has a top sheet disposed on a top side, a back sheet disposed on a back side, an absorbent body provided between the top sheet and the back sheet, and at least the absorbent body having top recessed portions recessed toward the back side from the top side and back recessed portions recessed toward the top side from the back side, and at least a part of top bottom portions of the top recessed portions are located at the same position as back bottom portions of the back recessed portions in a thickness direction or closer to the back side than the back bottom portions.

DETAILED DESCRIPTION (1) Outline of Embodiments

Description of the present specification and accompanying drawings clarify at least the following matters.

A absorbent sheet for pets according to one or more embodiments has a top sheet disposed on a top side, a back sheet disposed on a back side, an absorbent body provided between the top sheet and the back sheet, and at least the absorbent body having top recessed portions recessed toward the back side from the top side and back recessed portions recessed toward the top side from the back side, and at least a part (i.e., at least some) of top bottom portions of the top recessed portions are located at the same position as back bottom portions of the back recessed portions in a thickness direction or closer to the back side than the back bottom portions.

When a purchaser touches, on a top surface of the absorbent sheet for pets, a region overlapping the top recessed portion, it is possible to perceive the depth of the top recessed portion by texture. In addition, when a purchaser touches, on the top surface of the absorbent sheet for pets, a region overlapping the back recessed portion, it is easy to recess the region toward the back side due to a space generated by the back recessed portion. The space generated by the back recessed portion is as high as a space generated by the top recessed portion in a thickness direction or overlaps the space generated by the top recessed portion and is easily recessed when a purchaser touches the top recessed portion. Therefore, the purchaser easily feels the thickness of the absorbent sheet for pets by texture. Additionally, the purchaser is able to perceive the depth of the top recessed portion when visually confirming the top surface of the absorbent sheet for pets. The purchaser perceives the thickness of the absorbent sheet for pets by both texture and visual perception, and has secure feeling about the absorption performance.

According to one or more embodiments, the top bottom portions may be located closer to the back side than the back bottom portions, and the top recessed portions and the back recessed portions may be formed of embossed portions formed by compressing the absorbent body.

A region between the top recessed portion and the back recessed portion is pressed toward the back side at the time of forming the top recessed portion, while pressed toward the top side at the time of forming the back recessed portion. Therefore, the region between the top recessed portion and the back recessed portion is further compressed in the thickness direction, and the stiffness becomes high. Due to the fact that the stiffness of the region between the top recessed portion and the back recessed portion becomes high, a recessed shape by the top recessed portion and a recessed shape by the back recessed portion are easily maintained. Therefore, it becomes easier to maintain the thickness of the absorbent sheet for pets.

According to one or more embodiments, in a plan view of the absorbent sheet for pets, the absorbent sheet for pets may have first regions overlapping the top recessed portions in the thickness direction and second regions not overlapping the top recessed portions in the thickness direction, and at least a part of the absorbent body in the first region may further protrude toward the back side than the absorbent body in the second region.

The absorbent body protrudes toward the back side in a region overlapping the top recessed portion. The thickness of the absorbent body becomes thicker by the protrusion, and the thickness of the entire absorbent sheet for pets becomes thick. Therefore, a purchaser feels a larger thickness and easily feels safe about the absorption performance.

According to one or more embodiments, the top bottom portions may be located closer to the back side than a back surface of the absorbent body in the second regions.

The top bottom portions are located close to the back side than the back surface of the absorbent body in the second regions, and the top recessed portion has a depth as deep as the thickness of the second region. A purchaser easily perceives the depth of the top recessed portion, and secure feeling can be more easily obtained about the absorption performance.

According to one or more embodiments, the top recessed portions are configured to form a continuous or intermittent line, and the width of the line by the top recessed portions may be longer than the width of the second region located between the top recessed portions.

The width of the top recessed portion is longer than the width of the second region between the top recessed portions, and thus it is possible to make the top recessed portions noticeable. Therefore, a purchaser more easily recognizes the top recessed portions, and secure feeling can be more easily obtained about the absorption performance.

According to one or more embodiments, in the plan view of the absorbent sheet for pets, the absorbent sheet for pets may have third regions overlapping the back recessed portions in the thickness direction and fourth regions not overlapping the back recessed portions in the thickness direction, and at least a part of the absorbent body in the third region may further protrude toward the top side than the absorbent body in the fourth region.

The absorbent body protrudes toward the top side in a region overlapping the back recessed portion. The thickness of the absorbent body becomes thicker by the protrusion, and the thickness of the entire absorbent sheet for pets becomes thick. Therefore, a purchaser feels a larger thickness and easily feels safe about the absorption performance.

According to one or more embodiments, the back bottom portions may be located closer to the top side than a top surface of the absorbent body in the fourth region.

The back bottom portions are located closer to the top side than the top surface of the absorbent body in the fourth regions, and the back recessed portion has a depth as deep as the thickness of the fourth region. A purchaser easily perceives the depth of the back recessed portion, and secure feeling can be more easily obtained about the absorption performance.

According to one or more embodiments, the back recessed portions are configured to form a continuous or intermittent line and the width of the line by the back recessed portions may be longer than the width of the fourth region located between the back recessed portions.

The width of the back recessed portion is longer than the width of the fourth region between the back recessed portions. A purchaser more easily feels easiness in recessing by the back recessed portions, and secure feeling can be more easily obtained about the absorption performance.

According to one or more embodiments, the line may have a curved portion that does not branch.

The line having a curved portion does not continuously extend linearly, but extends in a plurality of directions and is easily noticeable compared with a linearly extending shape. In addition, in the curved portion that does not branch, each line becomes easily noticeable compared with in a curved portion that branches. Therefore, a purchaser more easily perceives the top recessed portions or the back recessed portions, and secure feeling can be more easily obtained about the absorption performance.

According to one or more embodiments, the lines may form a plurality of diagrams separated from each other.

When the top recessed portions or the back recessed portions form diagrams, the top recessed portions or the back recessed portions are locally disposed in a certain region, and it is possible to make the top recessed portions or the back recessed portions forming the diagrams noticeable respectively.

(2) Configuration of Absorbent Sheet for Pets

Hereinafter, an absorbent sheet for pets according to one or more embodiments will be described with reference to drawings. In the following description of the drawings, identical or similar portions will be given an identical or similar reference sign. The drawings are schematic, and attention needs to be paid to the fact that the ratio and the like of individual dimensions differ from the actual ones. Therefore, specific dimensions and the like need to be determined with reference to the following reference. In addition, dimensional relationships or ratios between portions are not always identical among the drawings.

In the present specification, "pets" broadly include vertebrate animals or invertebrate animals and typically include pet animals such as cats, dogs, rabbits, and hamsters.

Figure 1:
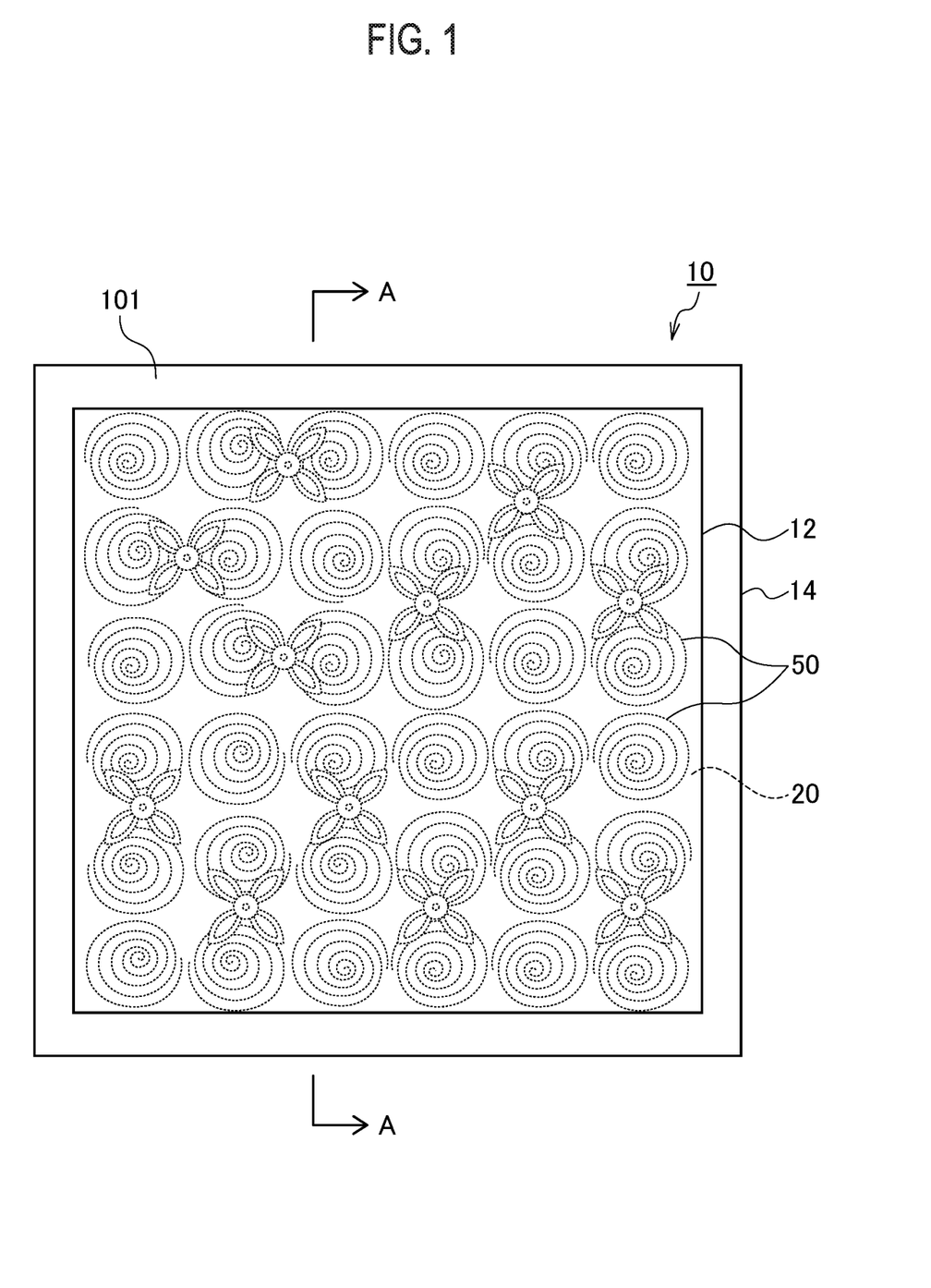
FIG. 1 is a plan view of an absorbent sheet for pets according to one or more embodiments seen from an excretion surface side.
Figure 2:
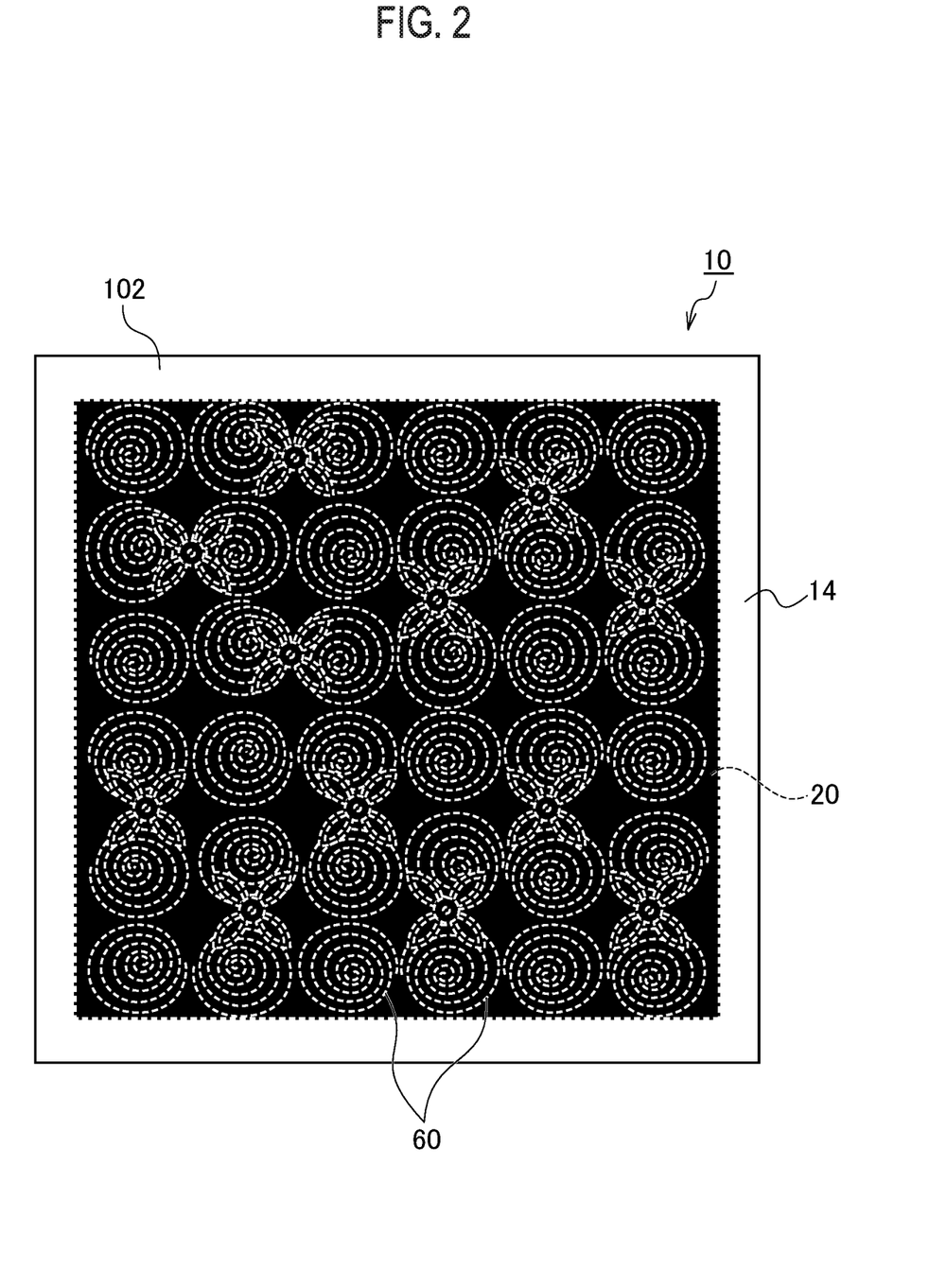
FIG. 2 is a plan view of the absorbent sheet for pets according to one or more embodiments seen from the excretion surface side.
Figure 3:
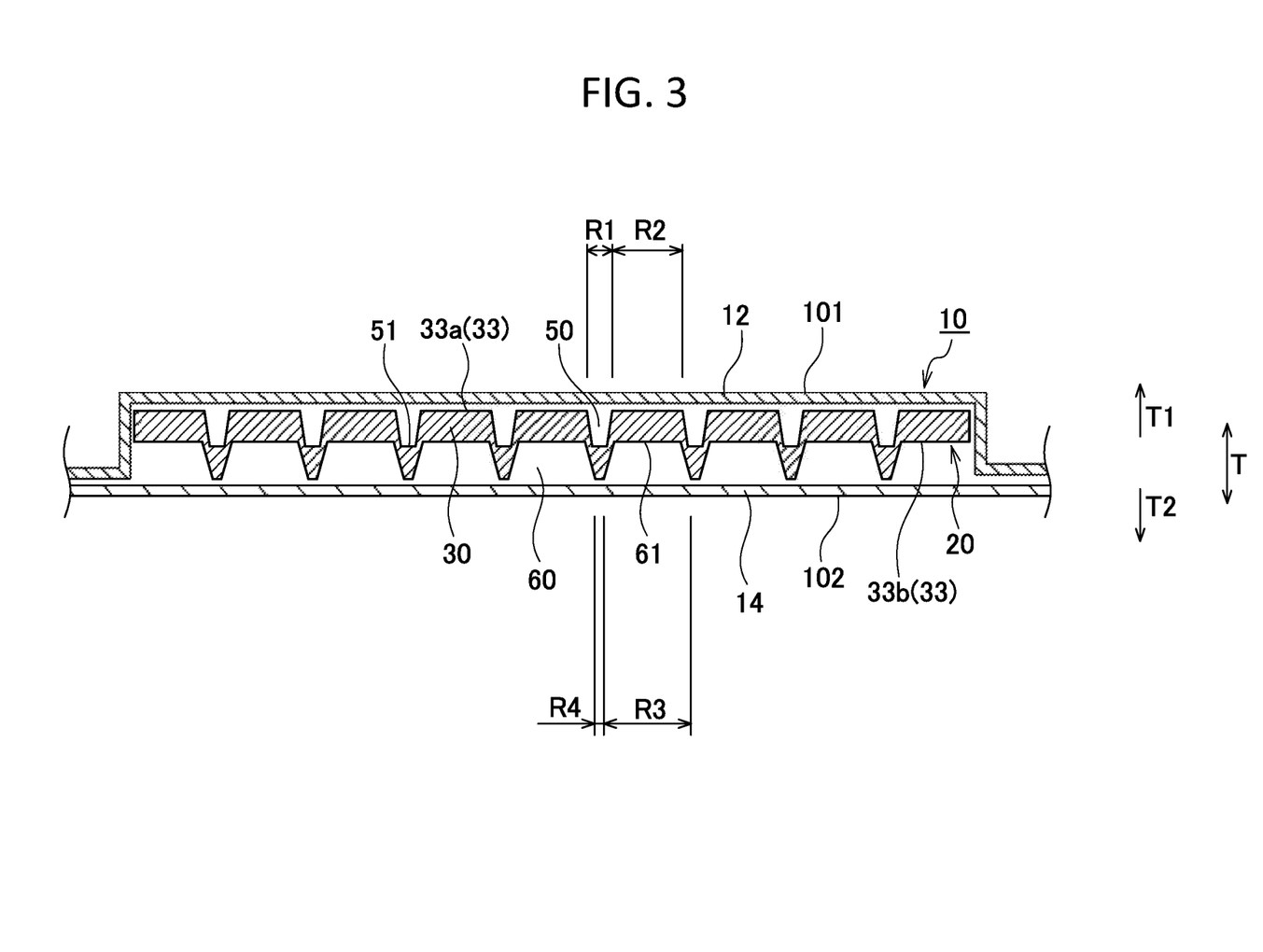
FIG. 3 is a schematic cross-sectional view of the absorbent sheet for pets along an A-A line shown in FIG. 1.
Figure 4:
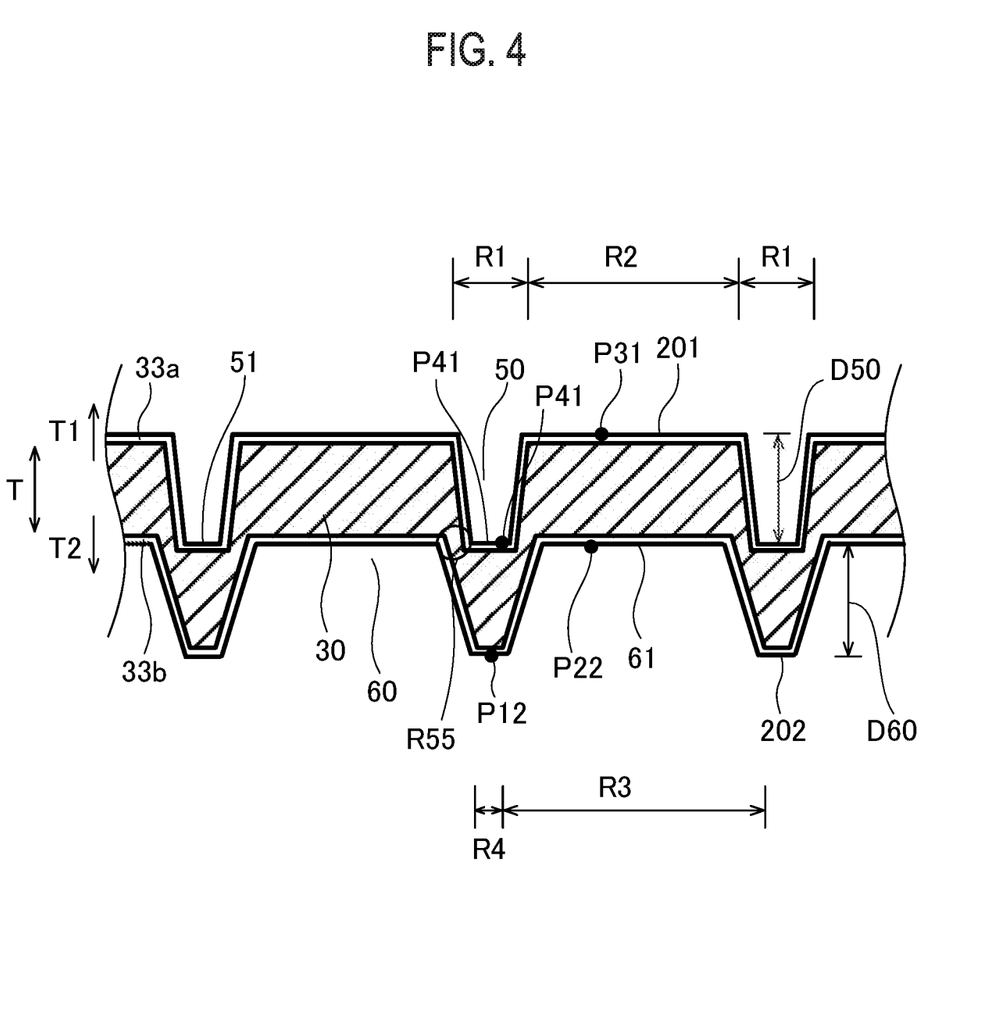
FIG. 4 is an enlarged cross-sectional view of an absorbent body shown in FIG. 3.

FIG. 1 and FIG. 2 are plan views of an absorbent sheet for pets according to one or more embodiments. FIG. 1 shows a state seen from an excretion surface side, and FIG. 2 shows a state seen from a non-excretion surface side. FIG. 3 is a schematic cross-sectional view of the absorbent sheet for pets along an A-A line shown in FIG. 1. FIG. 3 schematically shows a cross section of the absorbent sheet for pets and shows the decreased number of top recessed portions and back recessed portions by omitting some of the top recessed portions and the back recessed portions. FIG. 4 is an enlarged cross-sectional view of an absorbent body shown in FIG. 3. An absorbent sheet for pets 10 is generally a flat sheet. One surface of the absorbent sheet for pets 10 is an excretion surface that receives pets' excrement. In the one or more embodiments, the surface configuring the excretion surface will be described as a top surface 101, and a surface configuring a non-excretion surface will be described as a back surface 102. FIG. 3 shows a top side T1 and a back side T2 in a thickness direction T.

The absorbent sheet for pets 10 has a top sheet 12 disposed on the top side T1, a back sheet 14 disposed on the back side T2, and an absorbent body 20. The absorbent body 20 is provided between the top sheet 12 and the back sheet 14.

The top sheet 12 may be a liquid-permeable sheet that is permeable to liquid such as pets' excrement. The liquid-permeable sheet may be made of, for example, a liquid-permeable non-woven fabric or an opening film. The back sheet 14 may be a liquid-impermeable sheet that is not permeable to liquid such as pets' excrement. The back sheet 14 is not particularly limited and may be made of, for example, a resin film sheet. In one or more embodiments, a part of the back sheet 14 extends outside more than the top sheet 12. Therefore, in an outer circumferential portion of the absorbent sheet for pets 10, the back sheet 14 becomes visible from the top side T1.

An absorbent body 20 may include an absorbent core 30 and a core wrap 33 that wraps the absorbent core 30. The core wrap 33 may include a first core wrap 33a that covers the top side T1 of the absorbent core 30 and a second core wrap 33b that covers the back side T2 of the absorbent core 30 (refer to FIG. 4). At least one of the first core wrap 33a and the second core wrap 33b may cover side surfaces of the absorbent core 30.

The absorbent core 30 is not particularly limited and may include a hydrophilic fiber layer such as pulp, a superabsorbent polymer (SAP), or a combination thereof. The core wrap 33 is not particularly limited and can be made of, for example, liquid-permeable tissue.

The absorbent sheet for pets 10 has top recessed portions 50 recessed toward the back side T2 from the top side T1 and back recessed portions 60 recessed toward the top side T1 from the back side T2. The top recessed portion 50 has a shape that tapers toward the back side T2, and the back recessed portion 60 has a shape that tapers toward the top side T1. The top recessed portions 50 and the back recessed portions 60 may be formed in at least the absorbent body 20 and, in one or more embodiments, are formed in the absorbent core 30, the first core wrap 33a, and the second core wrap 33b, but may be formed only in the absorbent core.

The top recessed portion 50 has a top bottom portion 51 that is located closest to the back side T2 in the top recessed portion 50. A top surface 201 (a surface located on the top side) of the absorbent body 20 is configured with a top surface of the first core wrap 33a. In addition, the top recessed portions 50 are formed in the first core wrap 33a and the absorbent core 30. Therefore, the top bottom portions 51 are portions that are located closest to the back side T2 in the top surface of the first core wrap 33a. In a configuration in which the top recessed portions 50 are formed only in the absorbent core 30, the top bottom portions 51 are portions that are located closest to the back side T2 in the top surface of the absorbent core 30. A depth D50 of the top recessed portion 50 is the distance between the top bottom portion 51 and the top surface 201 of the absorbent body in a thickness direction T.

The back recessed portion 60 has a back bottom portion 61 that is located closest to the top side T1 in the back recessed portion 60. A back surface 202 (a surface located on the back side) of the absorbent body 20 is configured with a back surface of the second core wrap 33b. In addition, the back recessed portions 60 are formed in the second core wrap 33b and the absorbent core 30. Therefore, the back bottom portions 61 are portions that are located closest to the top side T1 in the back surface of the second core wrap 33b. In a configuration in which the back recessed portions 60 are formed only in the absorbent core 30, the back bottom portions 61 are portions that are located closest to the top side T1 in the back surface of the absorbent core 30. A depth D60 of the back recessed portion 60 is the distance between the back bottom portion 61 and the back surface 202 of the absorbent body in the thickness direction T.

At least a part (i.e., at least some) of the top bottom portions 51 of the top recessed portions 50 may be located at the same position as the back bottom portions 61 of the back recessed portions 60 in the thickness direction T or closer to the back side T2 than the back bottom portions 61. Spaces generated by the recesses of the top recessed portions 50 are formed on the top side T1 of the absorbent sheet for pets, and spaces generated by the recesses of the back recessed portions 60 are formed on the back side T2 of the absorbent sheet for pets. Therefore, when a purchaser touches, on the top surface 101 of the absorbent sheet for pets, a region overlapping the top recessed portion 50, the purchaser is able to perceive the depth of the top recessed portion 50 by texture. In addition, when a purchaser touches, on the top surface 101 of the absorbent sheet for pets, a region overlapping the back recessed portion 60, it is easy to recess the region toward the back side T2 due to the space generated by the back recessed portion 60. The space generated by the back recessed portion 60 is as high as the space generated by the top recessed portion 50 in the thickness direction or overlaps the space generated by the top recessed portion and is easily recessed when a purchaser touches the top recessed portion. Therefore, the purchaser easily feels the thickness of the absorbent sheet for pets by texture. Additionally, when seeing the top surface 101 of the absorbent sheet for pets, the purchaser is able to see the top recessed portion 50 through the top sheet 12 and perceive the depth of the top recessed portion 50. The purchaser perceives the thickness of the absorbent sheet for pets by both texture and visual perception, and has secure feeling about the absorption performance.

The shapes and positions of the top recessed portions and the back recessed portions may be confirmed using a well-known method. For example, it is possible to capture a cross section obtained by cutting the absorbent body 20 in the thickness direction using an electron microscope or the like and visually compare the shapes and the positions.

The top recessed portions 50 and the back recessed portions 60 may be configured with at least embossed portions obtained by compressing the absorbent body 20. This embossed portion may be formed by compressing only the absorbent core 30, may be formed by compressing the absorbent body 20 including the core wrap, or may be formed by compressing both the absorbent body 20 and the top sheet 12. In a case where the top recessed portions 50 and the back recessed portions 60 are configured with the embossed portions, the density of the absorbent body 20 at the position of the top recessed portion 50 is higher than the density of the absorbent body 20 around the top recessed portion 50, and the density of the absorbent body 20 at the position of the back recessed portion 60 is higher than the density of the absorbent body 20 around the back recessed portion 60.

Therefore, a region R55 (refer to FIG. 4) between the top recessed portion 50 and the back recessed portion 60 is pressed toward the back side T2 at the time of forming the top recessed portion 50 and pressed toward the top side T1 at the time of forming the back recessed portion 60. Therefore, the region R55 between the top recessed portion 50 and the back recessed portion 60 is further compressed in the thickness direction T, and the stiffness becomes high. Due to the fact that the stiffness of the region between the top recessed portion 50 and the back recessed portion 60 becomes high, a recessed shape by the top recessed portion 50 and a recessed shape by the back recessed portion 60 are easily maintained. Furthermore, the top bottom portion 51 is located closer to the back side T2 than the back bottom portion 61, whereby a region between the top bottom portion 51 and the back bottom portion 61 is, inversely, compressed in the thickness direction, and the stiffness easily becomes higher. The shapes of the top recessed portion 50 and the back recessed portion 60 are easily maintained, and a purchaser perceives the thickness of the absorbent sheet for pets by both texture and visual perception and easily feels safe about the absorption performance.

Alternatively, the top recessed portions 50 and the back recessed portions 60 may be configured by decreasing the weight per unit area of at least the absorbent body 20. In this case, the weight per unit area of the absorbent body 20 at the position of the top recessed portion 50 may be smaller than the weight per unit area of the absorbent body 20 around the top recessed portion 50, and the weight per unit area of the absorbent body 20 at the position of the back recessed portion 60 may be smaller than the weight per unit area of the absorbent body 20 around the back recessed portion 60.

As shown in FIG. 3 and FIG. 4, in a plan view, the absorbent sheet for pets has a first region R1 overlapping the top recessed portion 50 in the thickness direction, a second region R2 not overlapping the top recessed portion 50 in the thickness direction T, a third region R3 overlapping the back recessed portion 60 in the thickness direction T, a fourth region R4 not overlapping the back recessed portion 60 in the thickness direction T. The second region R2 is a region including, in a plan view, a region in which only the back recessed portion 60 is formed and regions in which neither the top recessed portion 50 nor the back recessed portion 60 are formed. In addition, the fourth region R4 is a region including, in the plan view, a region in which only the top recessed portion 50 is formed and regions in which neither the top recessed portion 50 nor the back recessed portion 60 are formed. In the absorbent sheet for pets 10 of one or more embodiments, the top recessed portion 50 and the back recessed portion 60 are adjacent to each other in the plan view. Therefore, the first region R1 of one or more embodiments is substantially the same region as the fourth region R4, and the second region R2 is substantially the same region as the third region R3. In an absorbent sheet for pets according to other embodiments, the top recessed portion 50 and the back recessed portion 60 may be disposed apart from each other in a plan view. This will be described below in detail.

At least a part of the absorbent body 20 in the first regions R1 may further protrude toward the back side T2 than the absorbent body 20 in the second region R2 in the thickness direction T. At least a part of the absorbent body 20 in the first regions R1 is a concept which includes a part of the absorbent body 20 in, among the plurality of first regions R1, a part of the first regions R1 and only a part of the absorbent body 20 in the thickness direction T (the back surface of the absorbent body) in an arbitrary first region R1. In more detail, the back surface (P12 shown in FIG. 4) of the absorbent body 20 in the first region R1 may further protrude toward the back side T2 than the back surface (P22 shown in FIG. 4) of the absorbent body in the second region. The absorbent body 20 protrudes toward the back side in regions overlapping the top recessed portions 50. The thickness of the absorbent body becomes thicker by the protrusion, and the thickness of the entire absorbent sheet for pets becomes thick. Therefore, a purchaser feels a larger thickness and easily feels safe about the absorption performance.

Furthermore, the top bottom portions 51 may be located closer to the back side T2 than the back surface P22 of the absorbent body 20 in the second region R2. The depth D50 of the top recessed portion 50 becomes equal to or larger than the thickness of the absorbent body 20 in the second region R2. A purchaser more easily perceives the depth of the top recessed portion 50, and secure feeling can be more easily obtained about the absorption performance.

At least a part of the absorbent body 20 in the third regions R3 may further protrude toward the top side T1 than the absorbent body 20 in the fourth region R4. At least a part of the absorbent body 20 in the third regions R3 is a concept which includes a part of the absorbent body 20 in, among the plurality of third regions R3, a part of the third regions R3 and only a part of the absorbent body 20 in the thickness direction T (the back surface of the absorbent body) in an arbitrary third region R3. In more detail, the top surface (P31 shown in FIG. 4) of the absorbent body in the third region R3 may further protrude toward the top side T1 than the top surface (P41 shown in FIG. 4) of the absorbent body in the fourth region R4. The absorbent body 20 protrudes toward the top side T1 in regions overlapping the back recessed portions 60. The thickness of the absorbent body becomes thicker by the protrusion, and the thickness of the entire absorbent sheet for pets becomes thick. Therefore, a purchaser feels a larger thickness and easily feels safe about the absorption performance.

Furthermore, the back bottom portions 61 may be located closer to the top side T1 than the top surface P41 of the absorbent body in the fourth region R4. The depth D60 of the back recessed portion 60 becomes equal to or larger than the thickness of the absorbent body 20 in the fourth region R4. A purchaser more easily perceives the depth of the back recessed portion 60, and secure feeling can be more easily obtained about the absorption performance.

At least one top recessed portion 50 and at least one back recessed portion 60 need to be provided on the absorbent body 20. In one or more embodiments, a number of point-like top recessed portions 50 are provided. These point-like top recessed portions 50 may be side by side so as to form an intermittent line IL. Instead, the top recessed portions 50 may extend in a linear or curved fashion so as to form a continuous line IL.

Figure 5:
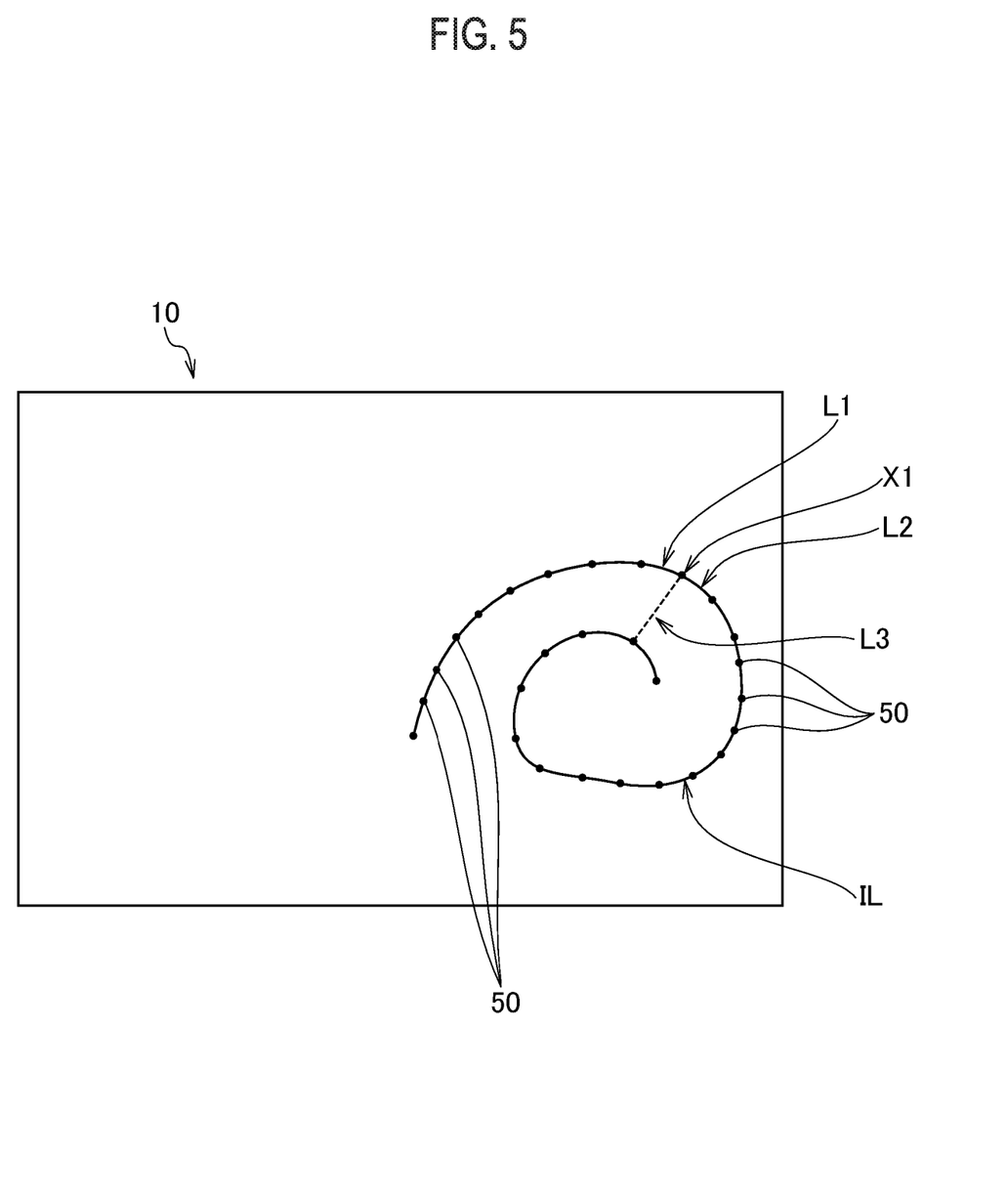
FIG. 5 is a view describing an example of a pattern of top recessed portions provided in the absorbent sheet for pets.

The continuous or intermittent line IL formed by the top recessed portions 50 will be described with reference to FIG. 5. FIG. 5 describes an example of a pattern of the top recessed portions 50 provided in the absorbent sheet for pets. The back recessed portions 60 may also form, similar to the top recessed portions, a continuous or intermittent line IL. The formation pattern of the continuous or intermittent line IL is identical for the top recessed portions and the back recessed portions, and the pattern of the top recessed portions to be described in one or more embodiments can also be employed for the back recessed portions.

The continuous or intermittent line IL formed by the top recessed portions 50 has a curved portion that does not branch. That is, in a region in which the line IL curves, the line IL does not branch into a plurality of lines. The "curved portion" may be a bent portion or a smoothly curved portion. However, the line formed by the top recessed portions 50 may include a branched curved portion. The line IL has a curved portion and thus does not continuously extend linearly, but extends in a plurality of directions and is easily noticeable compared with a linearly extending shape. In addition, in the curved portion that does not branch, each line becomes easily noticeable compared with in a curved portion that branches. Therefore, a purchaser more easily recognizes the recessed portions, and secure feeling can be more easily obtained about the absorption performance.

Here, the "continuous line" refers to a groove along which the top recessed portions 50 continuously extend. In addition, the "intermittent lines" are defined by imaginary lines connecting the top recessed portions 50 that are adjacent enough to be regarded as "intermittent lines" by the visual sense of a user. Specifically, the imaginary line is defined by a line (L1 or L2 in FIG. 5) connecting the top recessed portion 50 present at a position apart from the specific top recessed portion 50 (for example, X1 in FIG. 5) by a distance that is 1.5 times or less the distance between the specific top recessed portion 50 and the top recessed portion closest to the specific top recessed portion X1 and the specific top recessed portion 50. Therefore, a line (for example, L3 in FIG. 5) connecting the top recessed portions 50 apart from each other by a distance longer than 1.5 times the distance of the top recessed portion closest to the specific top recessed portion X1 does not form the intermittent line IL (imaginary line). In addition, as an example, the imaginary line may be defined by a line connecting the top recessed portions 50 apart at an interval of 1 cm or less and 5 mm or less. As described above, the top recessed portions 50 form an intermittent line, whereby the recessed portions become more noticeable by regions between the recessed portions in which the recessed portion is not formed.

A portion between an arbitrary line (L1 in FIG. 5) of the top recessed portions 50 and a second line (L2 in FIG. 5) apart from the arbitrary line at an interval may be the second region in which the top recessed portion 50 is not formed. A region in which the top recessed portion 50 is not formed is provided between a first line and the second line, and the first line and the second line are emphasized by the region. Therefore, a purchaser more easily recognizes the top recessed portions 50, and secure feeling can be more easily obtained about the absorption performance.

The width of the line IL by the top recessed portions 50 may be longer than the width of the second region (line L3 connecting the top recessed portions 50) located between the top recessed portions 50. The width of the top recessed portion 50 is longer than the width of the second region between the top recessed portions 50, and thus it is possible to make the top recessed portions 50 noticeable. Therefore, a purchaser more easily recognizes the top recessed portions 50, and secure feeling can be more easily obtained about the absorption performance. Additionally, in a case where the top recessed portions 50 form a diagram, it is possible to make the diagram look three-dimensionally and make the top recessed portions 50 more noticeable.

In addition, in a configuration in which the back recessed portions form a line, the width of the line IL by the back recessed portions 60 may be longer than the width of the second region (the line L3 connecting the top recessed portions 50) located between the back recessed portions 60. A purchaser more easily feels easiness in recessing by the back recessed portions, and secure feeling can be more easily obtained about the absorption performance.

Figure 6:
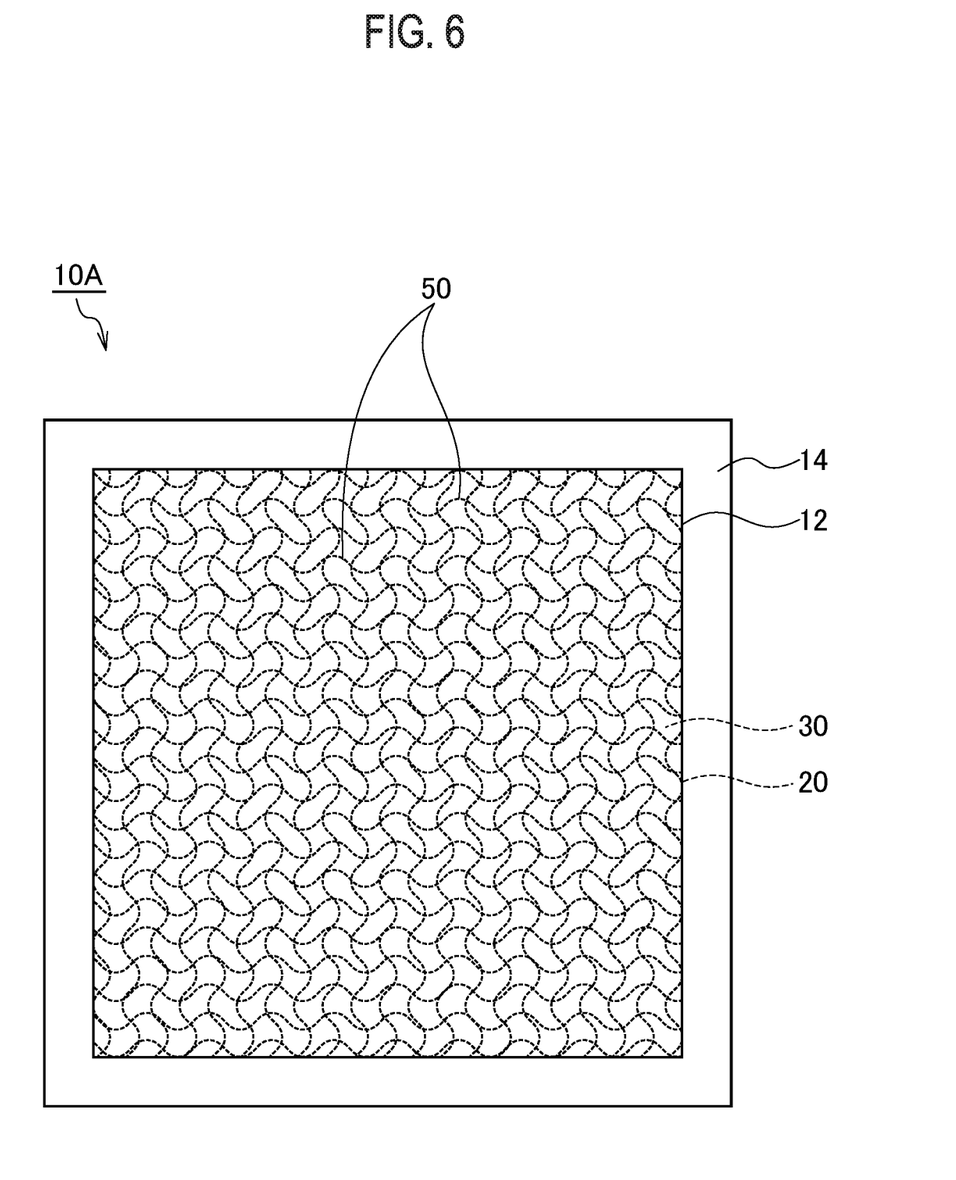
FIG. 6 is a plan view of another absorbent sheet for pets according to one or more embodiments.

Next, another absorbent sheet for pets according to one or more embodiments will be described. FIG. 6 is a plan view of an absorbent sheet for pets 10A. In the following description, the same elements are given the same reference signs and their descriptions will be omitted.

In FIG. 6, the top recessed portions 50 form an intermittent line IL, but may be alternatively configured to form a continuous line. In one or more embodiments, a plurality of lines IL formed by the top recessed portions 50 intersects each other. That is, the line IL has a plurality of branching points. Even when the line IL formed by the top recessed portions 50 branches as described above, the line IL also includes a curved portion that does not branch by curving. Even in the above-described aspect, the top recessed portions 50 do not continuously extend linearly, but extend in a plurality of directions and are easily noticeable compared with a linearly-extending shape. In addition, in the curved portion that does not branch, each line becomes easily noticeable compared with in a curved portion that branches. Therefore, a purchaser more easily recognizes the recessed portions, and secure feeling can be more easily obtained about the absorption performance.

Figure 7:
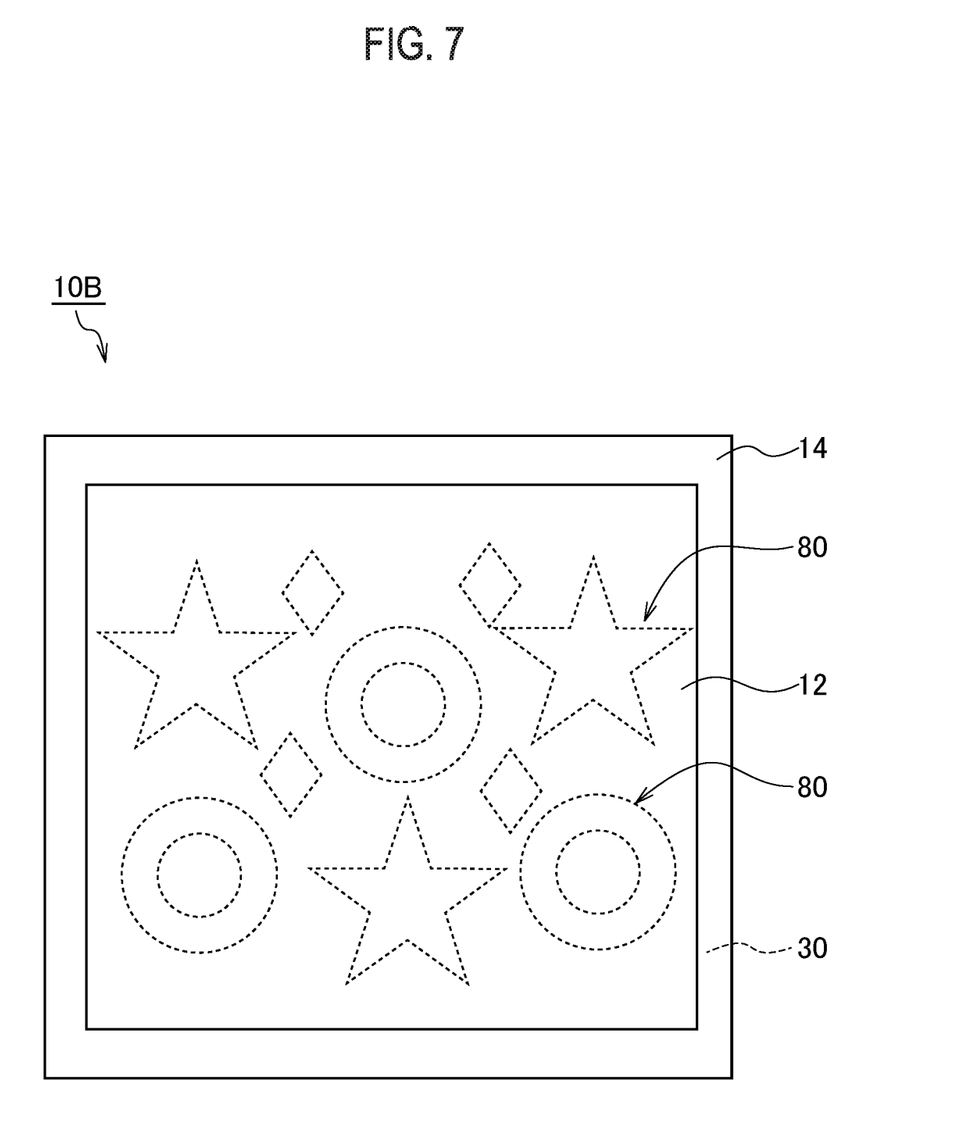
FIG. 7 is a plan view of another absorbent sheet for pets according to one or more embodiments.

Next, another absorbent sheet for pets according to one or more embodiments will be described. FIG. 7 is a plan view of an absorbent sheet for pets 10B. In FIG. 7, the top recessed portions 50 form an intermittent line, but may be alternatively configured to form a continuous line. In one or more embodiments, lines IL formed by the top recessed portions 50 form a plurality of diagrams 80 separated from each other. Therefore, the top recessed portions form diagrams, the top recessed portions are locally disposed in a certain region, and it is possible to make the top recessed portions forming the diagram noticeable respectively.

A diagram 80 formed by the top recessed portions 50 substantially or completely surrounds a region in the diagram 80. Here, "substantially surrounding" means that, when seen from a point in the diagram 80, the lines IL forming the diagram 80 are present in all directions. For example, a spiral diagram 80 substantially surrounds the region in the diagram 80.

In addition, "completely surrounding" means that the lines IL formed by the top recessed portions 50 form a closed curve. For example, a circular, polygonal, or star-like diagram 80 completely surrounds the region in the diagram 80. In addition, the diagram 80 formed by the top recessed portions 50 substantially or completely surrounds the region in the diagram 80, whereby the top recessed portions are locally disposed in a certain region, and it is possible to make the top recessed portions forming the diagram noticeable respectively.

Figure 8:
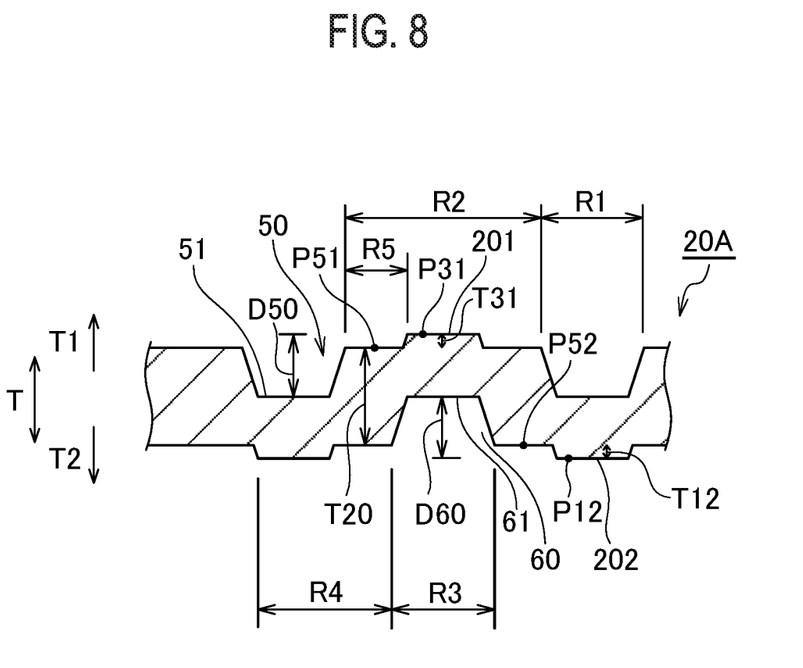
FIG. 8 is a schematic cross-sectional view of another absorbent sheet for pets according to one or more embodiments.

Next, another absorbent sheet for pets according to one or more embodiments will be described. FIG. 8 is a schematic cross-sectional view of an absorbent body 20A according to an absorbent sheet for pets. In this absorbent sheet, the top recessed portion 50 and the back recessed portion 60 are disposed apart from each other in a plan view. Therefore, the absorbent sheet for pets has a fifth region R5 in which neither the top recessed portion 50 nor the back recessed portion 60 are formed in a plan view.

The top surface (a surface located closest to the top side) 201 of the absorbent body 20A is provided in the third region R3. The top surface (P31 shown in FIG. 8) of the absorbent body in the third region R3 may further protrude toward the top side T1 than the top surface (P51 shown in FIG. 8) of the absorbent body 20A in the fifth region R5. In the fifth region R5, the top recessed portions 50 and the back recessed portions 60 are not formed, and the thickness does not substantially change before and after the formation of the embossed portions. A top surface P31 of the absorbent body in the third region R3 is pressed toward the top side T1 at the time of forming the back recessed portions 60 and further protrudes toward the top side T1 than the top surface P51 of the absorbent body in the fifth region R5 by a thickness T31. The top surface of the absorbent body is swollen toward the top side by the formation of the back recessed portions 60, whereby the thickness of the entire absorbent body becomes thicker. Therefore, a purchaser feels a larger thickness and easily feels safe about the absorption performance.

The back surface (a surface located closest to the back side) 202 of the absorbent body 20A is provided in the first region R1. The back surface (P12 shown in FIG. 8) of the absorbent body in the first region R1 may further protrude toward the back side T2 than the back surface (P52 shown in FIG. 8) of the absorbent body in the fifth region R5. The back surface P12 of the absorbent body 20 in the first region R1 is pressed toward the back side T2 at the time of forming the top recessed portions 50 and further protrudes toward the back side T2 than the back surface P52 of the absorbent body in the fifth region R5 by a thickness T12. The back surface of the absorbent body 20 is swollen toward the back side T2 by the formation of the top recessed portions 50, whereby the thickness of the entire absorbent body becomes thicker. Therefore, a purchaser feels a larger thickness and easily feels safe about the absorption performance.

When thickness of the absorbent body in a state before forming the top recessed portions 50 and the back recessed portions 60 is represented by T20, the thickness of the absorbent body 20 in a state in which the top recessed portions 50 and the back recessed portions 60 are formed becomes the original thickness T20+the thickness T31 swollen by the formation of the back recessed portions+the thickness T12 swollen by the formation of the top recessed portions.

Next, feeling safe about absorbability and the cushioning property were evaluated using the absorbent sheet for pets according to Example 1 to Example 3 and Comparative Example 1 to Comparative Example 4. In the absorbent sheet for pets according to Example 1 to Example 3, the top recessed portions and the back recessed portions are formed, and the top bottom portions are located at the same position as the back bottom portions in the thickness direction or the top bottom portions are located closer to the back side than the back bottom portions. In the absorbent sheet for pets according to Comparative Example 1, the top recessed portions and the back recessed portions are not formed. In the absorbent sheet for pets according to Comparative Example 2, only the top recessed portions are formed, and the back recessed portions are not formed. In the absorbent sheet for pets according to Comparative Examples 3 and 4, the top recessed portions and the back recessed portions are formed, and the top bottom portions are located closer to the top side than the back bottom portions.

Feeling safe about absorbability was evaluated on the basis of Comparative Example 1 by 10 examinees seeing the absorbent sheet for pets of Example 1 to Example 3 and Comparative Examples 1 to 4 and touching the top surfaces thereof. In visual evaluation, whether or not the absorbent sheet for pets looked thick was evaluated into three levels. In texture evaluation, whether or not the examinees felt thick when touching the top surface of the absorbent sheet for pets with a hand was evaluated into three levels. The total points by the 10 examinees are shown in Table 1.

1 point: Look thicker than Comparative Example 1 (feels thick)
0 point: Same as Comparative Example 1
−1 point: Look thinner than the comparative example (feels thin)

[Table 1]

As shown in Table 1, it was found that the absorbent sheet for pets according to Examples 1 to 3 looked thick to 90% or more of the examinees and were felt thick by 80% or more of the examinees. Therefore, it was found that, according to the absorbent sheet for pets according to Examples 1 to 3, the examinees more easily felt safe about absorbability.

Next, the cushioning property of the absorbent sheet for pets was evaluated. For the cushioning property, the thickness of the absorbent sheet for pets before weighted and the thickness of the absorbent sheet for pets after weighted were measured, and the compression ratio of the thickness after weighted to the thickness before weighted was computed. The absorbent sheet for pets was weighted by applying a weight of 3 kg to a 40 mm×60 mm area for one minute. The thickness was measured immediately after the weight was removed.

As shown in Table 1, it was found that the absorbent sheet for pets according to Example 1 to Example 3 were more easily compressed than the absorbent sheet for pets according to the comparative examples. As a result of intensive studies, the present applicant found that, when a pet steps on the absorbent sheet for pets and the absorbent sheet for pets is recessed, the pet easily recognizes that she is on an excretion place. It was found that, when an absorbent sheet for pets is easily compressed and has a favorable cushioning property as in the embodiments, pets easily recognize that they are on an excretion place, and users are also able to use the absorbent sheet for pets at ease.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

According to one or more embodiments, it is possible to provide an absorbent sheet for pets that allows a purchaser to perceive the thickness of the absorbent sheet for pets and easily feel safe about the absorption performance.

REFERENCE SIGNS LIST 10, 10A, 10B: absorbent sheet for pets
12: TOP SHEET
14: BACK SHEET
20, 20A: absorbent body
30: ABSORBENT CORE
33: CORE WRAP
50: TOP RECESSED PORTION
51: TOP BOTTOM PORTION
60: BACK RECESSED PORTION
61: BACK BOTTOM PORTION
80: DIAGRAM
IL: LINE
R1: FIRST REGION
R2: SECOND REGION
R3: THIRD REGION
R4: FOURTH REGION
R5: FIFTH REGION
R55: REGION
T: THICKNESS DIRECTION
T1: top SIDE
T2: BACK SIDE

The invention claimed is:

1. An absorbent sheet for pets comprising:
a top sheet disposed on a top side of the absorbent sheet;
a back sheet disposed on a back side of the absorbent sheet; and
an absorbent body disposed between the top sheet and the back sheet, the absorbent body comprising:
top recessed portions, each recessed toward the back side from the top side and comprising a top bottom portion; and
back recessed portions, each recessed toward the top side from the back side and comprising a back bottom portion, wherein
at least some of the top bottom portions are located either:

at the same position as some of the back bottom portions in a thickness direction, or closer to the back side than the back bottom portions in the thickness direction, in a plan view of the absorbent sheet, a first region of the absorbent sheet overlaps the top recessed portions in the thickness direction, and a second region of the absorbent sheet does not overlap the top recessed portions in the thickness direction, at least a part of the absorbent body in the first region protrudes further toward the back side than the absorbent body in the second region, the top recessed portions form an intermittent line having a width that is longer than a width of the second region located between the top recessed portions, and both the top recessed portions and the back recessed portions are embossed portions formed by compressing the absorbent body.

2. The absorbent sheet according to claim 1, wherein the top bottom portions are located closer to the back side than a back surface of the absorbent body in the second regions.

3. The absorbent sheet according to claim 1, wherein the top bottom portions are located closer to the back side than the back bottom portions in the thickness direction.

4. The absorbent sheet according to claim 1, wherein the line has a curved portion that does not branch.

5. The absorbent sheet for pets according to claim 1, wherein
the lines form a plurality of diagrams separated from each other.

6. An absorbent sheet for pets comprising:
a top sheet disposed on a top side of the absorbent sheet;
a back sheet disposed on a back side of the absorbent sheet; and
an absorbent body disposed between the top sheet and the back sheet, the absorbent body comprising:
top recessed portions, each recessed toward the back side from the top side and comprising a top bottom portion; and
back recessed portions, each recessed toward the top side from the back side and comprising a back bottom portion, wherein at least some of the top bottom portions are located either:
at the same position as some of the back bottom portions in a thickness direction, or closer to the back side than the back bottom portions in the thickness direction, in a plan view of the absorbent sheet, a third region of the absorbent sheet overlaps the back recessed portions in the thickness direction, and a fourth region of the absorbent sheet does not overlap the back recessed portions in the thickness direction, and at least a part of the absorbent body in the third region protrudes further toward the top side than the absorbent body in the fourth region, the back recessed portions form an intermittent line having a width that is longer than a width of the fourth region located between the back recessed portions, and both the top recessed portions and the back recessed portions are embossed portions formed by compressing the absorbent body.

7. The absorbent sheet according to claim 6, wherein the back bottom portions are located closer to the top side than a top surface of the absorbent body in the fourth region.

* * * * *